United States Patent [19]

Konrad et al.

[11] Patent Number: 4,499,188
[45] Date of Patent: Feb. 12, 1985

[54] BACTERIAL PRODUCTION OF HETEROLOGOUS POLYPEPTIDES UNDER THE CONTROL OF A REPRESSIBLE PROMOTER-OPERATOR

[75] Inventors: Michael W. Konrad, Alameda; David F. Mark, Hercules, both of Calif.

[73] Assignee: Cetus Corporation, Emeryville, Calif.

[21] Appl. No.: 375,098

[22] Filed: May 5, 1982

[51] Int. Cl.³ .................. C12P 21/02; C12P 21/00; C12N 15/00
[52] U.S. Cl. ........................... 435/70; 435/68; 435/172.3; 935/41
[58] Field of Search ................. 435/68-70, 435/172, 172.3; 935/41

[56] References Cited

U.S. PATENT DOCUMENTS 4,374,927 2/1983 Sninsky et al. .............. 435/172

FOREIGN PATENT DOCUMENTS 36776 9/1981 European Pat. Off. ........ 435/172

OTHER PUBLICATIONS

Mandelstam et al., Biochemistry of Bacterial Growth, John Wiley & Sons, pp. 159 & 160, (1982).
Derynck et al., Nature, vol. 285, pp. 542-546, Jun. 1980.
Taniguchi et al., Nature, vol. 285, pp. 546-549, Jun. 1980.
Edge et al., Nature, vol. 292, pp. 756-762, Aug. 1981.
Crawford et al., Ann. Rev. Biochem., vol. 49, pp. 163-195 (1980).

*Primary Examiner*—Alvin E. Tanenholtz
*Attorney, Agent, or Firm*—Albert P. Halluin; Janet E. Hasak; Thomas E. Ciotti

[57] ABSTRACT

A process for bacterially producing heterologous polypeptides, particularly those such as human IFN-$\beta$ that inhibit bacterial growth, in which bacteria that have been transformed to express the heterologous polypeptide under the control of a trp promoter-operator are cultivated in a known volume of medium containing an excess of a preferred carbon source such as glucose and a predetermined amount of tryptophan that corresponds approximately to the amount of tryptophan contained in the bacteria in the volume of medium at a predetermined elevated cellular density, whereby expression of the heterologous polypeptide is substantially repressed until the bacteria grow to approximately the predetermined elevated cellular density and is thereafter automatically derepressed to permit expression of the heterologous polypeptide.

10 Claims, 6 Drawing Figures

FIG. 1.

```
                LEU LEU LEU CYS PHE SER THR THR ALA LEU SER MET SER TYR ASN LEU
GGG GGG GGG GGG CTC CTG TTG TGC TTC TCC ACT ACA GCT CTT TCC ATG AGC TAC AAC TTG

61
LEU GLY PHE LEU GLN ARG SER SER ASN PHE GLN CYS GLN LYS LEU LEU TRP GLN LEU ASN
CTT GGA TTC CTA CAA AGA AGC AGC AAT TTT CAG TGT CAG AAG CTC CTG TGG CAA TTG AAT

121
GLY ARG LEU GLU TYR CYS LEU LYS ASP ARG MET ASN PHE ASP ILE PRO GLU GLU ILE LYS
GGG AGG CTT GAA TAT TGC CTC AAG GAC AGG ATG AAC TTT GAC ATC CCT GAG GAG ATT AAG

181
GLN LEU GLN GLN PHE GLN LYS GLU ASP ALA ALA LEU THR ILE TYR GLU MET LEU GLN ASN
CAG CTG CAG CAG TTC CAG AAG GAG GAC GCC GCA TTG ACC ATC TAT GAG ATG CTC CAG AAC

241
ILE PHE ALA ILE PHE ARG GLN ASP SER SER SER THR GLY TRP ASN GLU THR ILE VAL GLU
ATC TTT GCT ATT TTC AGA CAA GAT TCA TCT AGC ACT GGC TGG AAT GAG ACT ATT GTT GAG

301
ASN LEU LEU ALA ASN VAL TYR HIS GLN ILE ASN HIS LEU LYS THR VAL LEU GLU GLU LYS
AAC CTC CTG GCT AAT GTC TAT CAT CAG ATA AAC CAT CTG AAG ACA GTC CTG GAA GAA AAA

361
LEU GLU LYS GLU ASP PHE THR ARG GLY LYS LEU MET SER SER LEU HIS LEU LYS ARG TYR
CTG GAG AAA GAA GAT TTC ACC AGG GGA AAA CTC ATG AGC AGT CTG CAC CTG AAA AGA TAT

421
TYR GLY ARG ILE LEU HIS TYR LEU LYS ALA LYS GLU TYR SER HIS CYS ALA TRP THR ILE
TAT GGG AGG ATT CTG CAT TAC CTG AAG GCC AAG GAG TAC AGT CAC TGT GCC TGG ACC ATA

481
VAL ARG VAL GLU ILE LEU ARG ASN PHE TYR PHE ILE ASN ARG LEU THR GLY TYR LEU ARG
GTC AGA GTG GAA ATC CTA AGG AAC TTT TAC TTC ATT AAC AGA CTT ACA GGT TAC CTC CGA

541
ASN ***

AAC TGA AGA TC
```

```
  1
GAA TTC CGA CAT CAT AAC GGT TCT GGC AAA TAT TCT GAA ATG AGC TGT TGA CAA TTA ATC

61
                                                                        MET SER
ATC GAA CTA GTT AAC TAG TAC GCA AGT TCA CGT AAA AAG GGT ATC GAT AAG CTT ATG AGC

121
TYR ASN LEU LEU GLY PHE LEU GLN ARG SER SER ASN PHE GLN CYS GLN LYS LEU LEU TRP
TAC AAC TTG CTT GGA TTC CTA CAA AGA AGC AGC AAT TTT CAG TGT CAG AAG CTC CTG TGG

181
GLN LEU ASN GLY ARG LEU GLU TYR CYS LEU LYS ASP ARG MET ASN PHE ASP ILE PRO GLU
CAA TTG AAT GGG AGG CTT GAA TAT TGC CTC AAG GAC AGG ATG AAC TTT GAC ATC CCT GAG

241
GLU ILE LYS GLN LEU GLN GLN PHE GLN LYS GLU ASP ALA ALA LEU THR ILE TYR GLU MET
GAG ATT AAG CAG CTG CAG CAG TTC CAG AAG GAG GAC GCC GCA TTG ACC ATC TAT GAG ATG

301
LEU GLN ASN ILE PHE ALA ILE PHE ARG GLN ASP SER SER SER THR GLY TRP ASN GLU THR
CTC CAG AAC ATC TTT GCT ATT TTC AGA CAA GAT TCA TCT AGC ACT GGC TGG AAT GAG ACT

361
ILE VAL GLU ASN LEU LEU ALA ASN VAL TYR HIS GLN ILE ASN HIS LEU LYS THR VAL LEU
ATT GTT GAG AAC CTC CTG GCT AAT GTC TAT CAT CAG ATA AAC CAT CTG AAG ACA GTC CTG

421
GLU GLU LYS LEU GLU LYS GLU ASP PHE THR ARG GLY LYS LEU MET SER SER LEU HIS LEU
GAA GAA AAA CTG GAG AAA GAA GAT TTC ACC AGG GGA AAA CTC ATG AGC AGT CTG CAC CTG

481
LYS ARG TYR TYR GLY ARG ILE LEU HIS TYR LEU LYS ALA LYS GLU TYR SER HIS CYS ALA
AAA AGA TAT TAT GGG AGG ATT CTG CAT TAC CTG AAG GCC AAG GAG TAC AGT CAC TGT GCC

541
TRP THR ILE VAL ARG VAL GLU ILE LEU ARG ASN PHE TYR PHE ILE ASN ARG LEU THR GLY
TGG ACC ATA GTC AGA GTG GAA ATC CTA AGG AAC TTT TAC TTC ATT AAC AGA CTT ACA GGT

601
TYR LEU ARG ASN ***
TAC CTC CGA AAC TGA AGA TC
```

BACTERIAL PRODUCTION OF HETEROLOGOUS POLYPEPTIDES UNDER THE CONTROL OF A REPRESSIBLE PROMOTER-OPERATOR

DESCRIPTION

1. Technical Field

The invention is in the field of genetic engineering. More particularly it concerns a process for making heterologous polypeptides by cultivating certain genetically engineered bacteria under certain culture conditions.

2. Background Art

Various bacterial expression control DNA sequences have been used to control the expression of foreign (heterologous) polypeptides by transformed bacteria. One of these is the sequence that controls the expression of the structural genes of the tryptophan (trp) operon. Goeddel, et al, *Nucl Acid Res* (1980) 8:4057–4074, describe the construction of chimeric plasmids containing a trp control sequence linked to the IFN-β structural gene. *E.coli* transformed with these plasmids are reported to produce human IFN-β. Edman, et al, *Nature* (1981) 291:503–506, describe the construction of chimeric plasmids containing a portion of the trp control sequence linked to the structural genes that encode the Hepatitis B core antigen or a β-lactamase:Hepatitis B surface antigen fusion polypeptide. Expression of both of these polypeptides by transformed *E.coli* is reported.

European patent application No. 36776, published Sept. 30, 1981, describes plasmids containing a bacterial trp promoter-operator sequence linked to structural genes that encode somatostatin, human growth hormone, thymosin α 1, or polypeptides containing those heterologous polypeptides fused to a bacterial polypeptide. The plasmids lack a trp attenuator region. *E.coli* are transformed with these plasmids and transformants are grown in a medium to which tryptophan is added to repress the trp operator. Once the recombinant culture has grown to a level appropriate for industrial production of the foreign polypeptide the external source of tryptophan is removed, thereby derepressing the trp operator to allow expression of the foreign polypeptide. Only one technique for removing tryptophan from the medium is described. It involves diluting the tryptophan-rich medium in which the transformants are grown into a large volume of a medium containing no additive tryptophan. This dilution technique, while perhaps feasible on a laboratory scale, has significant disadvantages if practiced in a large scale cultivation. Among these disadvantages is a requirement either to measure the amount of tryptophan in the medium at the time of dilution in order to know how much to dilute or dilute many-fold and the necessity for additional equipment to add the diluent medium.

A main object of the invention is to provide a process for producing a heterologous polypeptide by the expression in bacteria of a structural gene coding for said polypeptide under the control of a repressible bacterial promoter-operator in which the bacteria are grown in a manner in which the culture medium is automatically depleted of additive repressor at a predetermined cellular density. This unique process requires no monitoring of repressor levels in the culture medium and no addition of diluent medium.

DISCLOSURE OF THE INVENTION

The invention is a process for bacterially producing a heterologous polypeptide comprising cultivating bacteria transformed to express said heterologous polypeptide under the control of a bacterial promoter-operator that (i) normally controls the expression of the structural genes that encode the polypeptides of a biosynthetic pathway that produces a product that is used by the bacteria in growth, (ii) is repressed by said product through activation of a repressor molecule by said product, and (iii) provides efficient expression of the structural genes under its control when derepressed in a predetermined volume of a culture medium containing an excess of essential nutrients and a predetermined amount of said product that corresponds approximately to the amount of said product that would be theoretically contained in the bacteria in said volume at a predetermined cellular density for a time sufficient to permit growth of the bacteria to said predetermined cellular density and expression of the heterologous polypeptide thereafter. Using this process the expression of the heterologous polypeptide is substantially repressed until the cellular density reaches approximately the predetermined cellular density and is thereafter derepressed automatically without external intervention to permit expression of the heterologous polypeptide.

This process is particularly advantageous for producing heterologous polypeptides, such as human IFN-β, that affect bacterial growth or viability adversely.

DESCRIPTION OF THE DRAWINGS

In the drawings:

FIG. 4 is a restriction map of the plasmid pβ1-trp described in Example 1, infra;

FIG. 5 is the DNA sequence between the EcoRI site and the XhoII site of pβ1-trp as shown in the enlargement of FIG. 4 and the amino acid sequence coresponding thereto.

MODES FOR CARRYING OUT THE INVENTION

As used herein the term "heterologous" refers to a structural gene not found in wild type bacteria and to polypeptide sequences not produced by such bacteria. Heterologous genes and polypeptides are typically eukaryotic genes and polypeptides.

As used herein the term "promoter-operator" denotes a sequence, native or engineered, of nucleotides that controls and regulates the expression of the linked structural genes that encode the polypeptides of a biosynthetic pathway. The nucleotide sequence begins with the promoter, includes the operator, the transcription start site, and the Shine-Delgarno sequence, and ends with the start codon for the expression of those polypeptides.

As used herein the term "structural gene" denotes that part of the relevant gene that encodes the amino acid sequence(s) for the expressed polypeptides under the control of the promoter-operator.

As used herein the term "expression" denotes the process by which a structural gene produces a polypeptide. It involves transcription of the relevant gene into messenger RNA (mRNA) and the translation of such mRNA into a polypeptide.

As used herein the term "vector" denotes the recombinant DNA molecules that include a heterologous structural gene under the control of a promoter-operator and: (1) are able to replicate autonomously in host bacteria, and (2) contain a marker function that allows selection of host cells transformed by the vector. This term is synonymous with the art term "cloning vehicle".

As used herein the term "transformed bacteria" denotes host bacteria that have been genetically engineered to produce a heterologous polypeptide under the control of a promoter-operator. Such bacteria are sometimes referred to herein as "transformants".

As used herein the term "repression" denotes the inactivation of the promoter such that the expression of structural genes controlled thereby is substantially inhibited.

As used herein the term "IFN" is synonomous with the term "interferon". Correspondingly, the terms "IFN-$\alpha$" and "IFN-$\beta$" are synonomous with the terms "leukocyte interferon" and "fibroblast interferon", respectively.

As used herein the term "human IFN-$\beta$" denotes IFN-$\beta$ that is produced by transformants that have been transformed with a vector that includes a human structural IFN-$\beta$ gene or a human structural IFN-$\beta$ gene that expresses an IFN-$\beta$ whose amino acid sequence is the same as or substantially homologous to native human IFN-$\beta$ under the control of a bacterial trp promoter-operator.

As used herein the term "turbidity" denotes cellular density as measured by optical density at 680 nm using a spectrophotometer or colorimeter.

The heterologous polypeptides that are made by the invention process will typically have industrial, agricultural, or medical utility. In most instances the polypeptides will be nonbacterial proteins such an eukaryotic cell proteins and viral proteins. Biologically active vertebrate cell proteins, especially human cell proteins, such as hormones, immunoregulatory molecules, antigens, and antibodies are of particular interest.

As indicated above the heterologous polypeptide is expressed under the control of a bacterial promoter-operator that normally controls the expression of a biosynthetic pathway that makes a product that is used by the bacteria in their growth. Such promoter-operators include the trp promoter-operator, the tyrA promoter-operator, the tyrB promoter-operator, and the pheA promoter-operator. These promoter-operators are repressed, respectively, by interaction of tryptophan, tyrosine, and phenyl alanine with their respective repressor proteins, the complex then binds to the respective operator and inactivates the promoter. The trp promoter-operator is preferred and, for convenience, the following description relates to the embodiment of the invention using that promoter-operator and tryptophan as a repressor.

The transformed bacteria that are employed in the invention process may be engineered using the procedures described by Goeddel, et al, supra, Edman, et al, supra, and European patent application Ser. No. 36776. These procedures basically involve (i) synthesizing or isolating the desired structural gene sequence that encodes the heterologous polypeptide, (ii) cloning the DNA sequence into an appropriate plasmid or viral vector at a site that is controlled by a bacterial trp promoter-operator, a ribosome binding site for the translation of the transcribed mRNA, and a translation start codon in the same translational reading frame as the structural gene, (iii) introducing the cloned sequence into competent bacterial cells, and (iv) selecting transformants either by a plasmid marker function or their ability to produce the heterologous polypeptide. *E.coli* are preferred for use in the process.

The heterologous polypeptide-producing transformants are introduced into a known volume of a culture medium that contains a predetermined amount of tryptophan that corresponds to the amount of tryptophan that would be theoretically contained in the bacteria in said volume at a predetermined cellular density. In addition to the added tryptophan, the medium will contain an excess of nutrient materials (other than tryptophan) that fulfill the cellular growth requirements of the bacteria thereby enabling the bacteria to grow and multiply to the predetermined cellular density. Such materials will include sources of carbon and nitrogen for synthesis of cellular components and energy, minerals (ions) such as sulfur ($SO_4^{-2}$), phosphorous ($PO_4^{-3}$), $Mg^{+2}$, $K^+$, and $Ca^{+2}$, amino acids, purines, pyrimidines, and vitamins. Trace elements will usually be contained in the water source for undefined media but must be added to defined media. Oxygen for facultative and aerobic bacteria will also be provided to the medium. In order to achieve maximum cellular densities, the cultivation will usually be carried out in a manner that enhances the area of the oxygen-liquid interface.

Important environmental factors affecting the cultivation include pH and temperature. The temperature will range between the minimal and maximum growth temperatures. Most bacteria exhibit maximum growth over a fairly narrow temperature range. For mesophilic bacteria, such as *E.coli*, the optimum temperature range is about 30° C. to about 40° C. Most organisms will tolerate hydrogen ion concentration ranging over several pH units. For pathogenic bacteria, such as *E.coli*, the tolerable pH lies in the range of about 6 to 8, with 6.5 being preferred.

Tryptophan is added to the medium before the cultivation is initiated in an amount that is correlated to the volume of culture medium and the approximate amount of tryptophan that would theoretically be in the cell mass in the volume at a predetermined cellular density. In the presence of excess preferred carbon source, such as glucose, the bacteria will use the tryptophan in the medium rather than producing it themselves for use in the production of cellular protein. While added tryptophan is present the bacteria repress expression of the heterologous polypeptide under the control of the trp promoter-operator. By initially adding a proper amount of tryptophan to the media the bacteria may be grown to a predetermined cellular density with the trp operator repressed. In order to determine this amount the volume of the medium must be known or determined, the amount of tryptophan per unit dry weight of the bacterial protein is determined experimentally or from published sources (for *E.coli* see *Studies of Biosynthesis in Eschericia Coli*, Roberts, et al, Carnegie Institution of Washington Publication 607 (1955), p28), and a desired cellular density is selected.

Cellular density may be expressed as grams (dry weight) of cells per unit volume of medium or in terms of the turbidity of the medium as measured with a photoelectric colorimeter (e.g. a Klett turbidometer) or spectrophotometer. Since turbidity is the most convenient measure of cellular density it is desirable to define the relationship between tryptophan addition and cellular density in terms of turbidity. For *E.coli* the relationship between turbidity and the grams (dry wt) of cells per unit volume of medium is linear, with one turbidity unit being approximately equal to 0.48 g (dry wt) cells per liter of medium. Using this relationship and the amount of tryptophan per unit weight (dry basis) of cells (approximately 11 mg tryptophan per g of cells for *E.coli*) the amount of tryptophan to be initially added to the medium per turbidity unit may be calculated. For *E.coli* that amount is:

$$\text{tryptophan (mg/l)} \approx 5.3 \times \text{turbidity} \quad (1)$$

While the bacteria may be grown to less than maximum density, they will usually be grown to substantially maximum cellular density, e.g. the density at which oxygen transfer becomes limiting. Such densities are normally characterized by turbidities in the range of about 10 to 100. In the case of *E.coli*, the amount of tryptophan to be initially added to the medium, determined from formula (1) above, will correspondingly range between 53 to 530 mg/l. When the turbidity of the medium reaches the predetermined turbidity, the amount of tryptophan added to the medium will have been consumed by the bacteria in producing cellular protein. The tryptophan is thus depleted automatically by cell growth and there is no need to intervene to dilute the medium or otherwise remove or monitor tryptophan in the medium. Once the tryptophan has been so depleted, the trp operator is derepressed and expression of the heterologous polypeptide is initiated.

The same cultivation conditions may be used in the heterologous polypeptide expression phase of the cultivation as were used in the exponential cell growth phase of the cultivation. The only exception to this is the absence of tryptophan in the culture medium during the expression phase. During the expression phase the growth rate will decrease if the heterologous polypeptide is one that affects cell growth/viability adversely. If the heterologous polypeptide does not so affect the cells, cell growth during the expression phase will be similar to normal growth. The duration of the expression phase may vary depending upon the bacteria, heterologous polypeptide, and cultivation conditions. The expression phase duration will usually be in the range of 1 to 5 hr.

After the expression phase the heterologous polypeptide is recovered from the cells and/or culture medium. In the case of IFN-β production by *E.coli*, the cells are harvested and the IFN-β is recovered therefrom. A preferred process for recovering human IFN-β from bacteria is disclosed in commonly owned, copending U.S. patent application Ser. No. 353,360 filed Mar. 1, 1982, titled "Process for Recovering Human IFN-β from a Transformed Microorganism" now U.S. Pat. No. 4,450,103. That recovery process involves disrupting the solubilizing the IFN-β into an aqueous medium with an anionic surfactant such as sodium dodecyl sulfate or sodium laurate and extracting the solubilized IFN-β from the aqueous medium with 2-butanol, 2-methyl-2-butanol, or mixtures thereof.

The following examples further describe the materials and methods used in carrying out the invention. The examples are not intended to limit the invention in any manner.

EXAMPLE 1

Construction of plasmid pβ1-trp for the direct expression of IFN-β under the control of trp promoter-operator The human IFN-β cDNA clone, 4El, was obtained by reverse transcriptase synthesis of cDNA using oligo-dT as primer, and as template, mRNA derived from human primary foreskin fibroblast cells. The cDNA was made double-stranded by the action of *E.coli* DNA polymerase I and nicked with Sl-nuclease. Homopolymeric tails were added to the 3'-termini of the ds cDNA by the enzyme terminal-transferase using dCTP as substrate. Similar homopolymeric tails were added to the 3'-termini of the plasmid pBR322 which had been linearized at the PstI site, using dGTP as substrate. The plasmid pBR322 and the ds cDNA were hybridized and transformed into *E.coli* K12. The clone, 4El, was identified by Grunstein-Hogness (PNAS (1975) 72:3961) colony hybridization screens using a $^{32}$P-labeled probe. Further characterization of the clone by restriction enzyme analysis gave the following results. PstI digestion of 4El yielded two insert fragments of about 600 bp and 200 bp in addition to a fragment corresponding to linear pBR322 DNA. BglII-PstI digestion of the same clone showed that the 600 bp PstI insert fragment can be further digested with BglII to yield two fragments of sizes 358 bp and 250 bp. HinfI digests of clone 4El showed that there are at least three HinfI sites in the insert fragment to generate three new fragments that are not present in pBR322.

Figure 1:
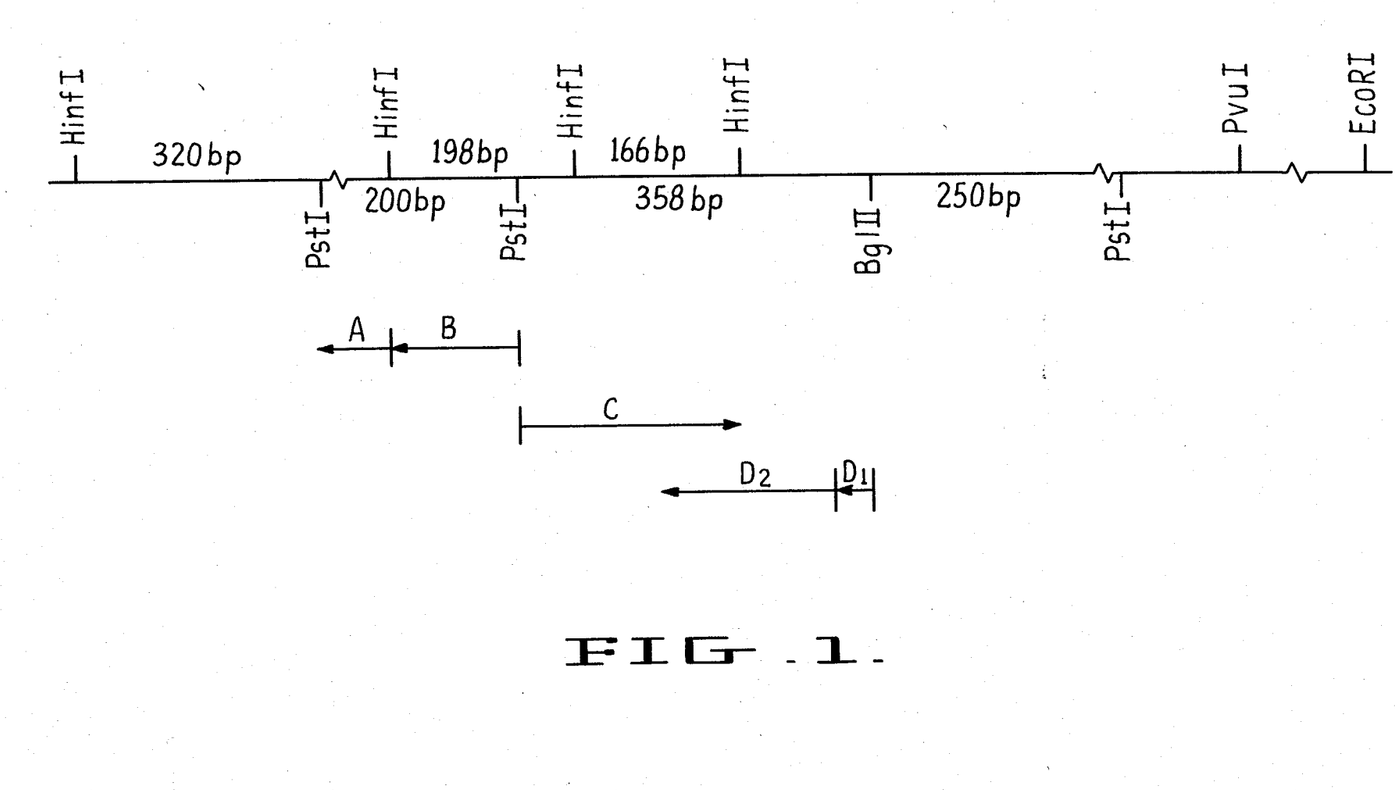
FIG. 1 is a restriction map of the human IFN-β cDNA clone described in Example 1, infra, and includes a diagram of the strategy used to determine the DNA sequence of that clone.
Figure 2:
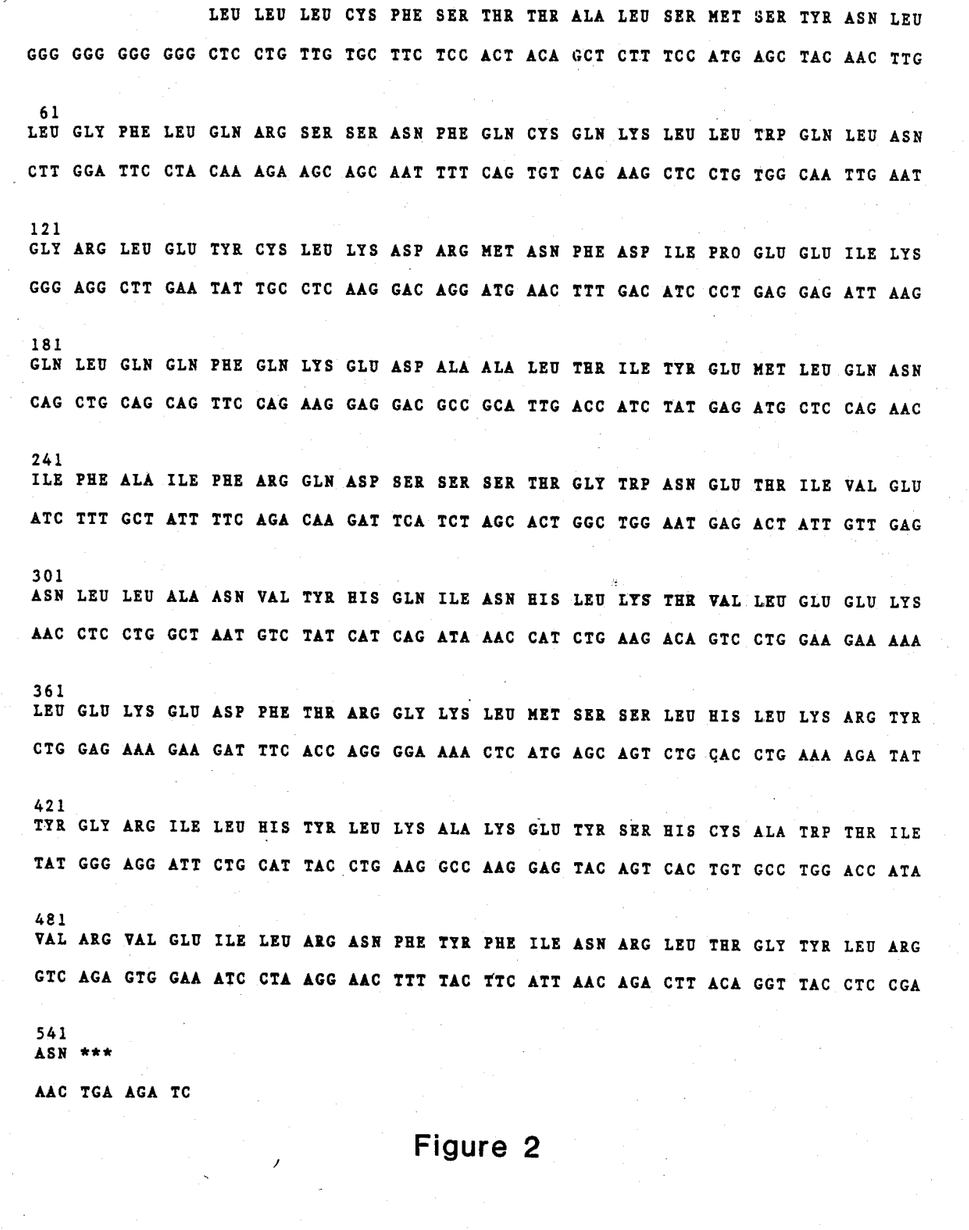
FIG. 2 is the DNA sequence of the coding strand of the coding region of the IFN-β cDNA clone described in Example 1, infra, and the amino acid sequence corresponding thereto.

FIG. 1 is a restriction map of clone 4El that includes a diagram showing the sequencing strategy used to sequence the coding region of the clone. The DNA sequence was obtained by a combination of Sanger's sequencing, (PNAS, (1977) 74:5463–5467) and Maxam-Gilbert sequencing (PNAS, (1977) 74:560–564). The Sanger technique was used to sequence fragment D2 whereas the remaining fragments (A, B, C, and D1) were sequenced by the Maxam-Gilbert method. The DNA sequence for the coding region of the IFN-β clone, 4El, and the corresponding predicted amino acid sequence are shown in FIG. 2.

Figure 3:
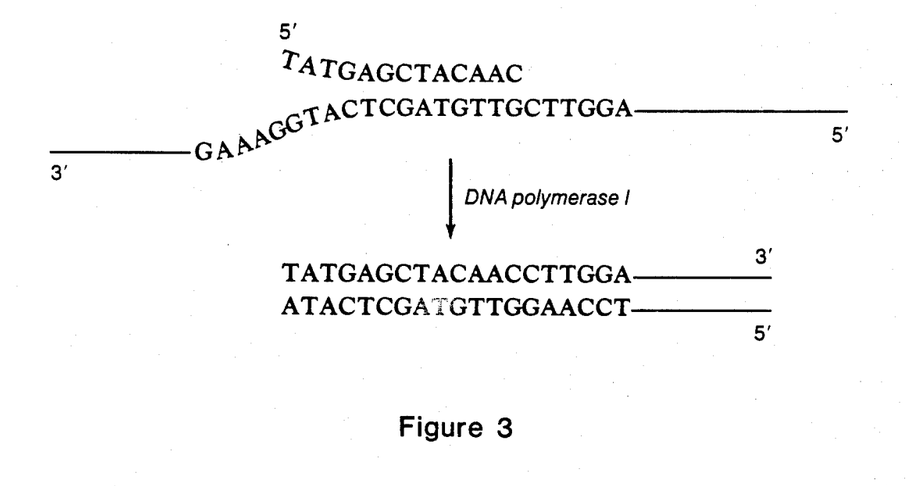
FIG. 3 depicts the subcloning of the IFN-β gene coding sequence described in Example 1.

The IFN-β gene coding sequence was subcloned by using a synthetic oligonucleotide primer (TATGAGC-TACAAC) and the enzyme DNA polymerase I to degrade DNA sequences 5' to the ATG codon which codes for the amino-terminal methionine of the mature interferon, thereby removing the DNA sequences coding for the leader peptide (FIG. 3). The repaired DNA was then subcloned into pBR322 at the repaired HindIII and at the BamHI sites. The BglII site in the IFN-β gene, just past the UGA termination codon, was used to ligate with the BamHI cohesive end in pBR322 to generate an XhoII site, while the repaired 5'-terminus of the IFN-β gene was blunt-end ligated to the repaired HindIII site; because the original primer has an extra thymidine nucleotide at its 5'-terminus, the HindIII site was regenerated. The resulting clone, pβ1-25, was analyzed by restriction analysis and DNA sequence analysis to confirm the presence of the HindIII site and the integrity of the initiation codon.

The *E.coli* trp promoter and ribosome binding site, which has previously been subcloned into pBR322, was ligated into pβ1-25 as an EcoRI-HindIII fragment.

Figure 4:
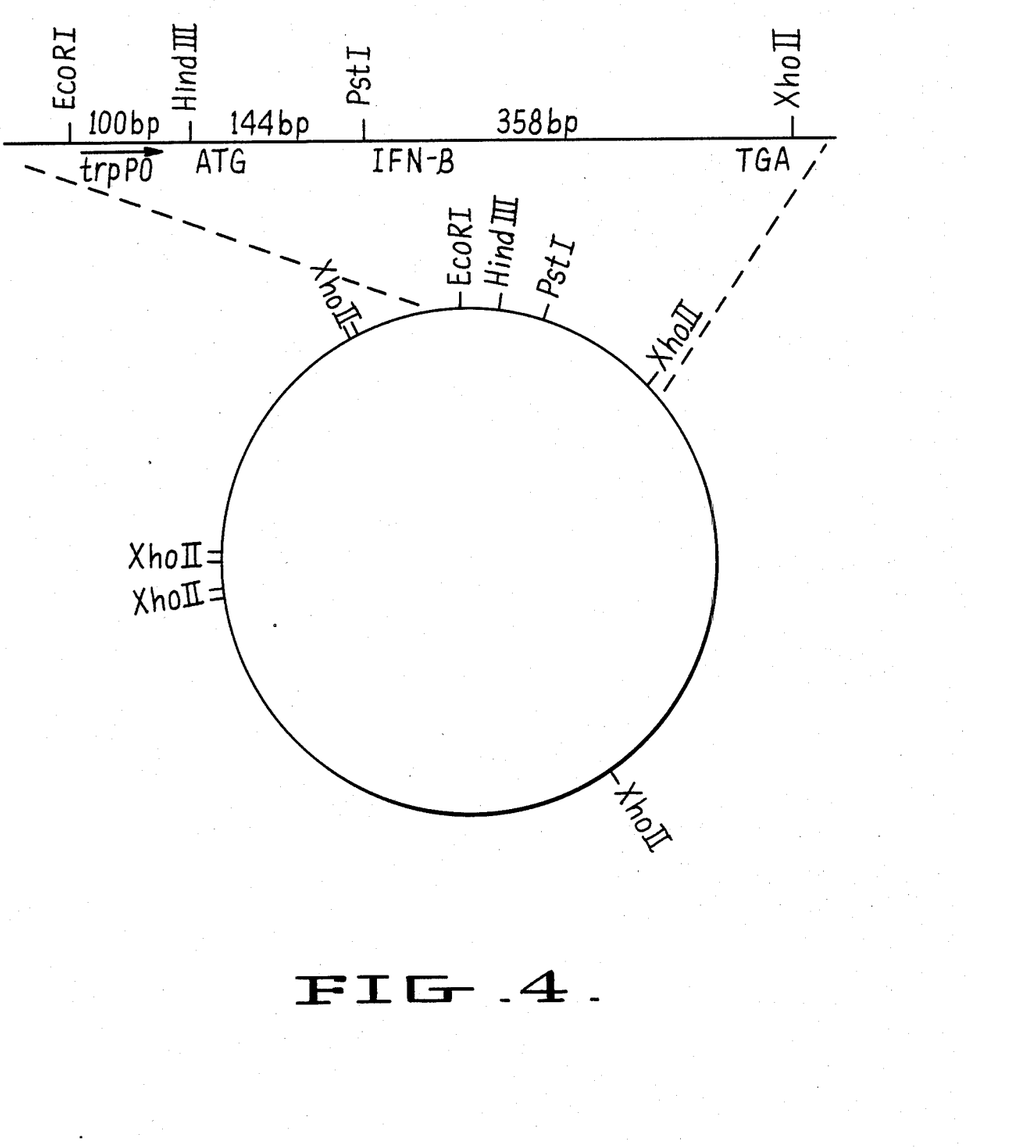

The resulting clone, pβ1-trp, was analyzed by restriction enzymes. FIG. 4 is a restriction map of pβ1-trp that includes an enlargement of the trp promoter operator region and the IFN-β coding sequence. FIG. 5 shows the nucleotide sequence between the EcoRI site and the XhoII site of pβ1-trp as shown in the enlargement of FIG. 4.

EXAMPLE 2

Effect of Tryptophan on growth of *E.coli* transformed with pβ1-trp

*E. coli* were transformed with pβ1-trp by conventional procedures (Mandell, M. and Higa, A. (1970) J Mol Biol 53:159) to produce a transformant line identified as MM294.

Twenty-five ml samples of MM294 growing in the medium described below were centrifuged at 10000×g for 10 min. The cells were resuspended in minimal medium containing (1) no tryptophan and (2) 20 γ/ml tryptophan. Turbidity readings of each media were taken at various time intervals spanning about a five and one-half hour period. These turbidities are tabulated below.

| Reading No | Turbidity (Klett units) | |
|---|---|---|
| | No Tryptophan | Tryptophan |
| 1 | 21 | 20 |
| 2 | 20 | 20 |
| 3 | 26 | 27 |
| 4 | 26 | 32 |
| 5 | 30 | 46 |
| 6 | 30 | 66 |
| 7 | 39 | 125 |

The culture medium comprised (concentrations indicated are sufficient for growth to 15 g/l dry weight):

| Base Medium | | Additives | |
|---|---|---|---|
| Ingredient | Concentration | Ingredient | Concentration |
| $(NH_4)_2SO_4$ | 72 mM | $FeSO_4.7H_2O$ | 72 μM |
| $KH_2PO_4$ | 21.6 mM | thiamine.HCl | 20 mg/l |
| $MgSO_4.7H_2O$ | 3 mM | ampicillin | 20 mg/l |
| Na citrate.$2H_2O$ | 1.5 mM | glucose | 30–50 g/l |
| $ZnSO_4.7H_2O$ | 45 μM | | |
| $MnSO_4.4H_2O$ | 45 μM | | |
| $CuSO_4.5H_2O$ | 4.5 μM | | |

These turbidity data show that the induction of IFN-β in the culture that did not contain tryptophan had an adverse effect on cell growth. In contrast, in the culture containing tryptophan the induction of IFN-β was repressed, thereby permitting the bacteria to grow at a characteristic exponential rate.

EXAMPLE 3

Cultivation of MM 294 Using Varying Initial Tryptophan Concentrations

MM 294 cell samples were grown and prepared as in Example 2. A laboratory fermenter was inoculated at a low density with a seed culture of these cells growing in minimal medium containing tryptophan at 70 mg/l and 364 mg/l. Turbidity readings were made periodically.

Figure 6:
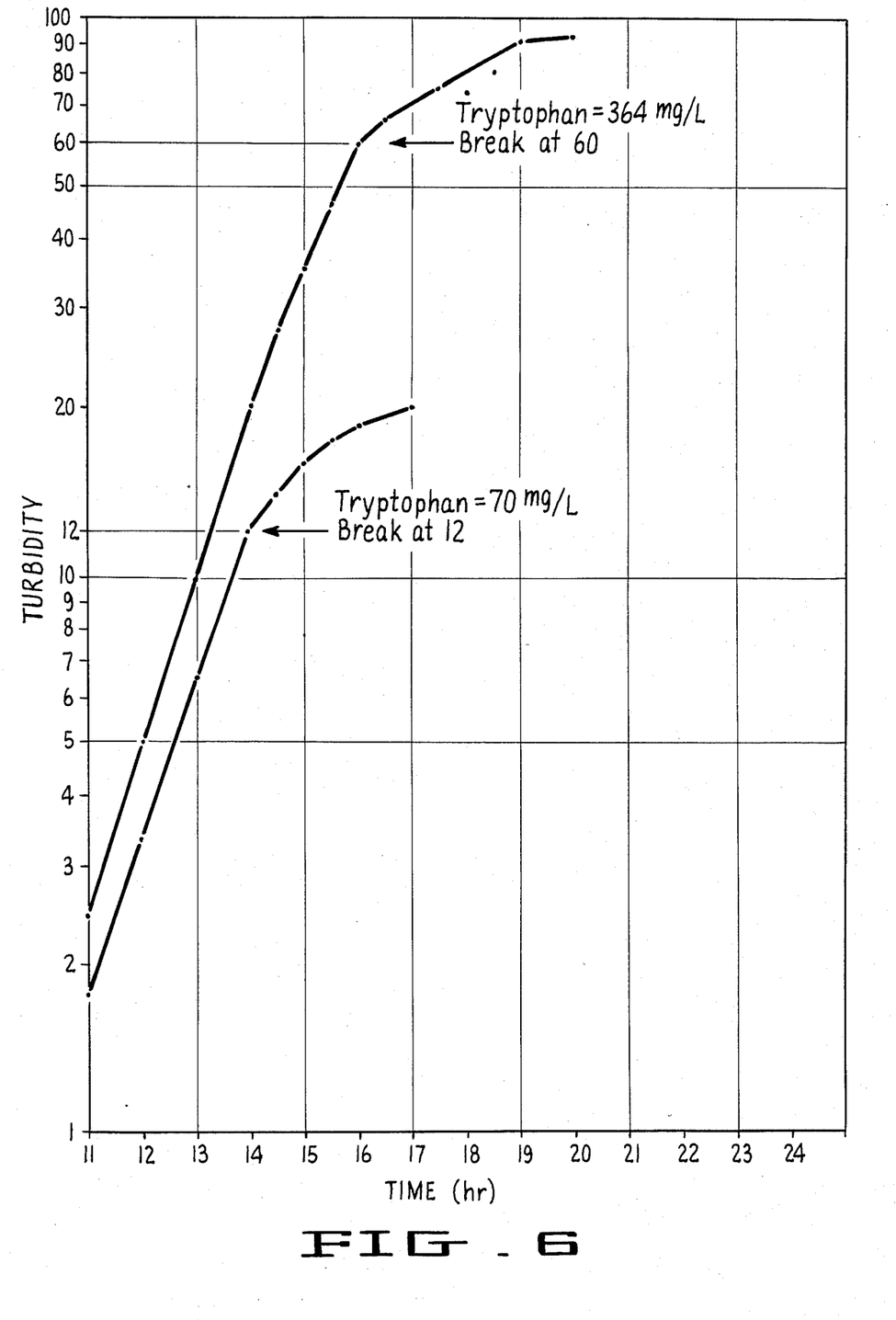
FIG. 6 is a graph of optical density versus time for the cultivations described in Example 3, infra.

FIG. 6 is a plot of logarithm of turbidity versus time for the two fermentations.

Using formula (1), supra, it was predicted that an initial tryptophan concentration of 70 mg/l would permit the cells to grow to a turbidity of about 13.4 before the tryptophan would be exhausted and the trp operator would be derepressed. It was similarly predicted that at 364 mg/l the turbidity at tryptophan exhaustion would be about 69. At these turbidities it was expected that cell growth would begin to be inhibited which would be reflected as breaks in the growth curves for the cultivations. As shown in FIG. 6 the observed breaks in the curves appear at about a turbidity of 12 for the 70 mg/l cultivation and at about 60 for the 364 mg/l cultivation. These observed values correspond reasonably well to the predicted values.

A similar cultivation of *E.coli* transformed to directly express IFN-α under control of the *E.coli* trp promoter-operator in a culture medium containing 25 mg tryptophan per 1 of medium showed no slowing of cellular growth through a turbidity of 20. Tryptophan was theoretically exhausted from the medium at a turbidity of about 4.7. These results indicate that IFN-α, unlike IFN-β, has no apparent adverse affect on *E.coli* growth and that the use of added tryptophan in such cultivations provides no advantageous results.

Modifications of the above described modes for carrying out the invention that are obvious to those of ordinary skill in the biochemical engineering field or related technologies are intended to be within the scope of the following claims.

We claim:

1. A process for bacterially producing a heterologous polypeptide comprising cultivating bacteria transformed to express said heterologous polypeptide under the control of a bacterial promoteroperator that
   (i) normally controls the expression of the structural genes that encode the polypeptides of a biosynthetic pathway that produces a product that is used by the bacteria in growth,
   (ii) is repressed by said product through activation of a repressor molecule by said product, and
   (iii) provides efficient expression of the structural genes under its control when derepressed in a volume of a culture medium containing an excess of essential nutrients and a predetermined amount of said product that corresponds approximately to the amount of said product contained in the bacteria in said volume at a predetermined, elevated cellular density for a time sufficient to permit growth of the bacteria to the predetermined cellular density and expression of the heterologous polypeptide thereafter.

2. The process of claim 1 wherein the promoter-operator is the trp promoter-operator and the product is tryptophan.

3. The process of claim 1 or 2 wherein the heterologous polypeptide affects bacterial growth or viability adversely.

4. The process of claim 1 or 2 wherein the heterologous polypeptide is human IFN-β.

5. The process of claim 1 or 2 wherein the heterologous polypeptide is human IFN-β, the bacteria are *E.coli*, and the trp promoter-operator is the *E.coli* trp promoter-operator.

6. The process of claim 5 wherein the predetermined amount of tryptophan is defined by the formula:

mg tryptophan/l of medium $\approx 5.3 \times$ predetermined turbidity.

7. The process of claim 1 or 2 wherein the predetermined elevated cellular density is substantially maximum cellular density.

8. The process of claim 2 wherein the predetermined elevated cellular density as measured by the turbidity of the medium is in the range of about 10 to about 100.

9. The process of claim 8 wherein the bacteria are *E.coli* and the predetermined amount of tryptophan is in the corresponding range of about 53 mg/l of medium to about 530 mg/l of medium.

10. The process of claim 9 wherein the bacteria have been transformed with the plasmid p$\beta$1-trp.

* * * * *